US008979909B2

(12) United States Patent
DiMatteo (10) Patent No.: US 8,979,909 B2
(45) Date of Patent: Mar. 17, 2015

(54) TISSUE REPAIR SUTURE PLATES AND METHODS OF USE

(75) Inventor: Kristian DiMatteo, Waltham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 172 days.

(21) Appl. No.: 13/537,670

(22) Filed: Jun. 29, 2012

(65) Prior Publication Data

US 2014/0005729 A1    Jan. 2, 2014

(51) Int. Cl.
*A61B 17/88* (2006.01)
*A61B 17/80* (2006.01)
*A61B 17/04* (2006.01)
*A61B 17/00* (2006.01)

(52) U.S. Cl.
CPC ........... *A61B 17/809* (2013.01); *A61B 17/0401* (2013.01); *A61B 17/8052* (2013.01); *A61B 17/8085* (2013.01); *A61B 2017/00004* (2013.01); *A61B 2017/0409* (2013.01); *A61B 2017/044* (2013.01)
USPC ............................ 606/281; 606/280; 606/232

(58) Field of Classification Search
USPC ............. 606/70–71, 139, 228, 232, 280–281, 606/283–286, 297–298
See application file for complete search history.

(56) References Cited

U.S. PATENT DOCUMENTS

| | | | | |
|---|---|---|---|---|
| 4,769,034 A | * | 9/1988 | Poley | 606/166 |
| 5,860,978 A | | 1/1999 | McDevitt et al. | |
| 6,514,274 B1 | * | 2/2003 | Boucher et al. | 606/232 |
| 6,592,609 B1 | * | 7/2003 | Bonutti | 606/232 |
| 7,727,241 B2 | * | 6/2010 | Gorensek et al. | 606/99 |
| 8,114,128 B2 | | 2/2012 | Cauldwell et al. | |
| 8,632,590 B2 | * | 1/2014 | Cauthen et al. | 623/17.11 |
| 2003/0078465 A1 | | 4/2003 | Pai et al. | |
| 2005/0107795 A1 | * | 5/2005 | Morris et al. | 606/69 |
| 2006/0241617 A1 | | 10/2006 | Holloway et al. | |
| 2007/0288023 A1 | * | 12/2007 | Pellegrino et al. | 606/72 |
| 2008/0015710 A1 | | 1/2008 | Hays et al. | |
| 2008/0147064 A1 | | 6/2008 | Cauldwell et al. | |
| 2009/0076544 A1 | | 3/2009 | DiMatteo et al. | |
| 2009/0076545 A1 | | 3/2009 | DiMatteo et al. | |
| 2009/0216270 A1 | * | 8/2009 | Humphrey | 606/232 |
| 2009/0287246 A1 | | 11/2009 | Cauldwell et al. | |
| 2009/0318960 A1 | * | 12/2009 | Burkhart | 606/228 |
| 2010/0016899 A1 | * | 1/2010 | Gelfand | 606/280 |

FOREIGN PATENT DOCUMENTS

WO          2007/021893 A1    2/2007
WO    WO 2009095451 A1 *    8/2009    ............. A61B 17/80

OTHER PUBLICATIONS

U.S. Appl. No. 13/331,322 entitled "Systems and Methods for Repairing Tissue" filed Dec. 21, 2011.

* cited by examiner

*Primary Examiner* — Nicholas Woodall
*Assistant Examiner* — Larry E Waggle, Jr.

(57) ABSTRACT

Tissue repair suture plates and methods of use are provided which can, in general, allow soft tissue to be secured to bone. In one embodiment, a tissue repair suture plate can include a plurality of openings formed therethrough that can each be configured to have one or more sutures passed therethrough. Each of the sutures can be configured to be coupled to a soft tissue to be positioned against bone for healing thereagainst such that the soft tissue can have multiple sutures coupled thereto at different areas thereof. One or more bone fixation elements can be coupled to the plate and can be configured to attach the plate to the bone. The plate can be configured to move between a first configuration in which the plate has a first maximum length and a second configuration in which the plate has a second, greater maximum length.

19 Claims, 8 Drawing Sheets

TISSUE REPAIR SUTURE PLATES AND METHODS OF USE

FIELD OF THE INVENTION

The present invention relates generally to methods and devices for reattaching soft tissue to bone, such as in repair of torn rotator cuffs.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities. In the case of a partial detachment, the injury will frequently heal itself, if given sufficient time and if care is taken not to expose the injury to further undue stress. In the case of complete detachment, however, surgery may be needed to re-attach the soft tissue to its associated bone or bones.

Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone. In soft tissue re-attachment procedures utilizing suture anchors, an anchor-receiving hole is generally first drilled in the bone at the desired point of tissue re-attachment. Then a suture anchor is deployed in the hole with a portion of one or more sutures secured to the anchor, with the free end(s) of the suture extending out of the bone. The free ends of the suture are passed through or around the soft tissue and are used to tie the soft tissue securely to the bone.

With any of the above techniques, it is generally desirable to increase the number of fixation points where tissue is secured to bone in order to increase the surface area of the tissue drawn into contact with the bone, which can facilitate healing, and to decrease the load on the tissue at any one point, which can help prevent tissue damage. In the case of soft tissue reattachment with suture anchors, one approach to increasing the number of fixation points is to increase the number of suture anchors. Too many suture anchors, however, can compromise the integrity of the bone due to the amount of bone material that must be impinged and/or removed to install the suture anchors. Another approach to increasing the number of tissue fixation points that does not require an increase in the number of suture anchors is to attach multiple suture strands to each anchor. However, the multiple suture strands extending from an anchor must generally be passed through the same region of tissue because if tissue too remote from the anchor is drawn towards the anchor, the tissue may pucker or fold. Because the multiple suture strands are passed through the same region of tissue, the load on the tissue is not appreciably reduced.

Accordingly, there remains a need for improved methods and devices for attaching tissue to bone.

SUMMARY OF THE INVENTION

The present invention generally provides tissue repair suture plates and methods of use. In one aspect, a surgical method is provided that includes affixing an elongate plate to bone in proximity to detached soft tissue using one or more bone fixation elements coupled to the plate and extending into the bone, the plate having a plurality of openings, and a plurality of suture strands extending from the plate along a length thereof. Each of the plurality of openings has at least one of the plurality of suture strands extending therethrough. The method also includes passing the suture strands through portions of the detached soft tissue and drawing the detached soft tissue into contact with the plate and the bone, and securing the soft tissue with the suture strands at a desired position in contact with the plate and the bone.

The elongate plate can be formed from any one or more materials, such as by being formed from at least one of a flexible mesh, a bioabsorbable material, and an osteoconductive material.

The method can have any number of variations. For example, the soft tissue can be secured to the plate and bone by at least one of knotting and tying one or more of the suture strands. For another example, one or more of the suture strands can be secured to the one or more bone fixation elements. In yet another example, the suture strands can be attached to and extend from the elongate plate before affixing the elongate plate to bone, and/or after delivering the elongate plate into a body of a patient including the bone to which the elongate plate is affixed. In another example, the elongate plate can be delivered into a body of a patient to a tissue reattachment site in a delivery configuration in which the plate is folded, and prior to affixing the elongate plate, the plate can be unfolded and oriented in a substantially linear configuration such that a bone contacting surface formed along a length of one surface of the plate is substantially in contact with the bone.

In another aspect, a surgical plate is provided that includes an elongate plate member having bone fixation elements coupled to opposed ends of the plate, at least one hinge region formed between the anchors, the hinge region extending across a width of the plate, and a plurality of openings formed through the plate member and extending from a bone contacting surface thereof to a soft tissue seating surface thereof.

The surgical plate can have a number of variations. For example, the openings can include a plurality of slots formed along a length of the elongate plate member. For another example, one or more suture strands can be slidably disposed within the slots. For yet another example, a plurality of strands of suture can extend from the elongate plate member and be configured to secure soft tissue to the tissue seating surface of the elongate plate member. The strands of suture can be secured through one or more of the openings, each strand of suture having a portion abutting a land region of the elongate plate member located between adjacent openings, having a first suture limb extending from a first one of the adjacent openings, and a having second suture limb extending from a second one of the adjacent openings. For yet another variation, the elongate plate member can have an intermediate portion between the opposed ends, and the width of the plate at the opposed ends can be greater than the width of the plate at the intermediate portion. The surgical plate can also include bone fixation elements configured to be seated in bores formed in the opposed ends of the plate so as to couple the bone fixation elements to the bone, the bone fixation elements being configured to be fixated to bone. The bone fixation elements can include one or more of a suture, a suture bushing, and an anchor. In another example, the bone fixation elements can be integrally formed with the plate.

The elongate plate member can also be formed from a variety of materials. For example, the elongate plate member can be bioabsorbable and can be made from a material selected from the group consisting of poly-L-lactide (PLLA), poly(lactic-co-glycolic acid) (PLGA), poly-L/D-lactide (PLDLA), polyglyconate, polylactic acid (PLA), polyglycolic acid (PGA), polycaprolactone (PCL), polydioxanone (PDO), and trimethylene carbonate (TMC). For yet another example, the elongate plate member can be osteoconductive and can be at least one of made from and coated with a material selected from the group consisting of biphasic calcium phosphate, hydroxyapatite, α-tricalcium phosphate, β-tricalcium phosphate, bioactive glass, calcium phosphate, calcium sulfate, calcium carbonate, xenogeneic and allogeneic bone material.

In another aspect, a soft tissue anchoring system is provided that includes one or more anchors having a head and at least one bone engaging surface feature on a shank thereof, an elongate plate member having one or more bores formed therein for receiving the one or more anchors, and a plurality of openings extending therethrough, and a plurality of suture strands extending from the plate member.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary tissue repair suture plates, and methods of use are provided. In general, the tissue repair suture plates, also referred to herein as plates, and tissue repair suture plate systems can allow for attaching tissue to bone, such as in repair of torn rotator cuffs. The plates can allow at least one suture to be coupled to a tissue to be secured to bone without requiring the at least one suture to be secured to an element, e.g., a suture anchor, inserted into the bone, which can help prevent weakening, damaging, and/or otherwise adversely affecting the bone. In one embodiment, a plate can include a plurality of openings formed therethrough that can each be configured to have one or more sutures passed therethrough such that a plurality of sutures can be coupled to the plate. Each of the plurality of sutures can be configured to be coupled to a soft tissue, e.g., passed therethrough, to be positioned against bone for healing thereagainst such that the soft tissue can have multiple sutures coupled thereto at different areas of the soft tissue. Each of the plurality of sutures can be tensioned to optimize contact of the soft tissue with bone. The plate's openings can therefore allow multiple sutures to be coupled to the soft tissue without requiring the sutures to be coupled to elements inserted into bone, e.g., suture anchors, which can help reduce damage to the bone. Because the sutures can be coupled to the soft tissue at different points, and can therefore be tensioned at different points of the soft tissue, a load can be more evenly distributed across the soft tissue throughout healing than with sutures all passed through a same point of tissue. Such load balancing can help facilitate contact of the soft tissue with bone and/or can help reduce chances of any of the sutures cutting through (e.g., cheese wiring through) the soft tissue. Additionally, one or more bone fixation elements, e.g., a suture anchor, a suture bushing or eyelet, a suture line-lock, etc., can be coupled to the plate, such as by being integrally formed therewith or by being inserted through one or more bores formed through the plate. The one or more bone fixation elements can be configured to attach the plate to bone, thereby helping to hold the plate, the sutures, and the tissue in a substantially fixed position relative to the bone, which can facilitate healing. The one or more bone fixation elements can each have one or more sutures coupled thereto. Each of these sutures can be coupled to the soft tissue coupled to the sutures passed through the openings and can be tensioned similar to that discussed above, thereby further improving load balancing. The plate can therefore allow a soft tissue to have a greater total number of points having suture coupled thereto, e.g., passed therethrough, than a total number of bone fixation elements coupled to, e.g., advanced into, the bone, which can help reduce damage to the bone and/or help facilitate load balancing. In other words, a total number of sutures coupled to the soft tissue can be greater than a total number of bone fixation elements coupled to the plate.

The plate can be configured to move between a first configuration in which the plate has a first maximum length and a second configuration in which the plate has a second maximum length that is greater than the first maximum length. For non-limiting example, the plate can be configured to be folded in the first configuration and unfolded in the second configuration. The plate can be configured to be advanced into a patient's body in the first configuration and to move to the second configuration when at least partially disposed within the patient's body, which can allow the plate to be advanced into the patient's body through a relatively small access opening, e.g., incision, thereby reducing patient healing time, improving cosmesis, reducing patient tissue trauma, and/or achieving other benefits of minimally invasive surgery that will be appreciated by a person skilled in the art. Also by being configured to be introduced into a patient's body in a smaller size than when the plate is implanted within the patient, e.g., the smaller first configuration versus the larger second configuration, the plate can achieve benefit(s) of a minimally invasive surgical procedure while allowing a larger surface area of the plate to contact tissue and bone within the patient, which can facilitate healing, than would be possible with a plate that cannot move to a larger size for implantation within a patient's body.

The tissue repair suture plates disclosed herein can be formed in any way, e.g., molded or woven, from any one or more materials, such as a biocompatible material(s) safe for use in a patient's body. In one embodiment, the tissue repair suture plate can be formed, e.g., molded, from a biocompatible polymer. A variety of biocompatible polymers can be used to form the biocompatible tissue repair suture plates, such as polyetheretherketone (PEEK), polylactic acid (PLA), and Biocryl® Rapide available from DePuy Mitek of Raynham, Mass. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring.

In an exemplary embodiment, the plates can be formed from and/or coated with one or more osteoconductive and/or bioabsorbable materials, although in some embodiments the plates can be made from one or more non-bioabsorbable materials. By being formed from a bioabsorbable material(s), the plate can be configured to naturally degrade and be absorbed within a patient's body such that a surgical procedure would not be necessary to remove the plate from the patient's body after soft tissue has healed. Being formed from and/or coated with an osteoconductive material(s) can allow the plates to facilitate healing, e.g., by encouraging bone growth. Exemplary bioabsorbable materials include poly-L-lactide (PLLA), poly(lactic-co-glycolic acid) (PLGA), poly-L/D-lactide (PLDLA), polyglyconate, polylactic acid (PLA), polyglycolic acid (PGA), polycaprolactone (PCL), polydioxanone (PDO), and trimethylene carbonate (TMC). Exemplary osteoconductive materials include biphasic calcium phosphate, hydroxyapatite, α-tricalcium phosphate, β-tricalcium phosphate, bioactive glass, calcium phosphate, calcium sulfate, calcium carbonate, xenogeneic and allogeneic bone material.

The tissue repair suture plates disclosed herein can be formed from a mesh material. In an exemplary embodiment, the mesh material can be flexible. The mesh material can be fluid pervious or impervious, and the mesh material can be treated to increase or decrease its frictional interaction with tissue, as will be appreciated by a person skilled in the art. For non-limiting example, the mesh material can be treated to increase its frictional interaction with soft tissue, thereby facilitating healing by helping to position the soft tissue in optimal contact with bone.

The mesh material can include a reinforcing material including any absorbable or non-absorbable textile having, for non-limiting example, woven, knitted, warped knitted e.g., lace-like), non-woven, and braided structures. In any of the above structures, mechanical properties of the mesh material can be altered by changing the density or texture of the material, the type of knit or weave of the mesh material, the thickness of the mesh material, or by embedding particles in the material. The mechanical properties of the mesh material can also be altered by creating sites within the mesh material where the fibers are physically bonded with each other or physically bonded with another agent, such as, for example, an adhesive or a polymer. The fibers used to make the reinforcing component can be, e.g., monofilaments, yarns, threads, braids, or bundles of fibers. These fibers can be made of any one or more biocompatible materials, as will be appreciated by a person skilled in the art.

As mentioned above, the tissue repair suture plates can be formed from one or more non-bioabsorbable materials. Exemplary embodiments of non-bioabsorbable materials include biocompatible metals such as stainless steel, cobalt chrome, titanium and titanium alloys, and bioinert ceramic particles (e.g., alumina, zirconia, and calcium sulfate particles). Other exemplary embodiments of non-bioabsorbable materials include polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., polyvinylidene fluoride, polytetrafluoroethylene, and hexafluoropropylene).

FIGS. 1-4 illustrate one exemplary embodiment of a surgical plate 10 configured to aid in securing a tissue to bone by allowing at least one suture to be coupled to the tissue without requiring the at least one suture to be secured to a bone fixation element, e.g., a suture anchor, inserted into the bone. The plate 10 can have a variety of sizes, shapes, and configurations. As shown in the illustrated embodiment, the plate 10 can be an elongate plate having one or more openings 12, also referred to herein as "bores," formed therethrough that can each be configured to seat a bone fixation element, e.g., an anchor 82, therein. The one or more bone fixation elements can be configured to attach the plate 10 to bone. The plate 10 can also include a plurality of additional openings 14 each configured to have one or more sutures 86 passed therethrough. The plate 10 can also include one or more land regions 18 positioned between adjacent ones of the additional openings 14 that can be configured to facilitate coupling the one or more sutures 86 to the plate 10, which can facilitate securing a tissue to the plate 10. The plate 10 can optionally include one or more hinges 16 that, as discussed in more detail below, can be configured to allow the plate 10 to be movable between folded and elongated configurations.

In the illustrated embodiment, the plate 10 is substantially rigid, e.g., formed from one or more substantially rigid materials. In other embodiments, as mentioned above, a plate can be substantially flexible, e.g., formed from one or more substantially flexible materials, such that the plate can be deformable. A flexible, deformable plate can facilitate movement of the plate between folded and expanded configurations, as discussed further below, and can help the plate dynamically conform to a shape of a bone surface to which the plate is adjacently implanted and dynamically conform to a tissue surface, as also discussed further below.

The plate 10 is elongate and has a substantially rectangular shape in the illustrated embodiment, but the plate can be elongate and have another shape, e.g., square, oval, dogbone-shaped, irregularly-shaped, etc. The plate 10 can have a tissue seating surface 20 and a bone contacting surface 22 on an opposite side of the plate 10 from the tissue seating surface 20, e.g., the tissue seating surface 20 being on a top of the plate 10 and the bone contacting surface 22 being on a bottom of the plate 10. The tissue seating surface 20 and the bone contacting surface 22 can each be substantially flat, as in the illustrated embodiment, although the tissue seating surface 20 and/or the bone contacting surface 22 can have non-flat profiles. For non-limiting example, a plate can have a curved or other non-flat bone contacting surface, which can help the plate approximate a curved shape of a bone surface at a tissue reattachment site. If a plate is substantially flexible, the plate can be configured to dynamically conform to a curved or other non-flat shape of a bone surface, but if a plate is substantially rigid, having a non-flat bone contacting surface can help maximize contact with the bone, which can facilitate healing, e.g., by increased surface area of tissue in contact with bone and/or by promoting bone growth into the plate caused in part by minimizing void space between a bone surface and the bone conforming surface. Similarly, a substantially flexible plate can be configured to dynamically conform to a curved or other non-flat shape of a tissue, but if a plate is substantially rigid, having a non-flat tissue seating surface can help maximize contact with the tissue, which can facilitate healing.

The plate 10 can have a variety of dimensions. In an exemplary embodiment, the plate 10 can have a substantially non-varying thickness T. The thickness T of the plate 10 can be different depending on the plate's application and materials of construction. The thickness T can be in a range of about 1 mm to 2 mm, which can allow the plate's thickness T to approximate a thickness of a bone cortex. In another embodiment, the thickness T can be less than about 0.5 mm, which can facilitate positioning the plate 10 sub-flush in bone. Generally, the larger the plate's thickness T, the greater the strength of suture attachment to the plate 10, also depending on a strength of the material(s) forming the plate 10. In some embodiments, a plate can have a thickness that varies along a length of the plate and/or along a width of the plate. For non-limiting example, a bone contacting surface of the plate can have a shape that a the shape of a bone surface, e.g., be curved, while a tissue seating surface of the plate can be substantially flat such that the thickness of the plate varies along the length thereof in accordance with the bone contacting surface's shape. The plate 10 can have any length L and any width W. In an exemplary embodiment, the length L of the plate 10 can be less than about 20 mm, e.g., in a range of about 10 mm to 20 mm, e.g., about 18 mm, etc., and the width W can be less than about 10 mm, e.g., about 5.5 mm, in a range of about 6 mm to 7 mm, etc. The width W in the illustrated embodiment is non-varying along the length L of the plate 10, but the width W can vary in different portions along the length L, e.g., when the plate has a non-rectangular or non-square shape, such as ovular or dogbone-shaped.

The openings 12 formed in the plate 10 can each have a variety of sizes, shapes, and configurations. The plate 10 can include any number of openings 12. In the exemplary embodiment illustrated in FIGS. 1-4, the plate 10 includes two openings 12. The openings 12 can be located at opposed ends of the plate 10 along the length L thereof, which can facilitate load balancing and help maximize contact of the plate 10 with bone and tissue. The openings 12 can be longitudinally aligned with one another along the length L of the plate 10, which can help improve load balancing. The openings 12 can also be centered lengthwise and/or widthwise in the plate 10, which can facilitate load balancing and/or can help prevent the plate 10 from buckling when anchor(s) are inserted therethrough. If a plate includes more than two openings, each pair of openings formed through the plate can be longitudinally aligned with one another. If a plate includes a single opening, the opening can be centered both lengthwise and widthwise along the plate, which can facilitate load balancing, although the single opening can be offset lengthwise and/or widthwise.

Figure 3:
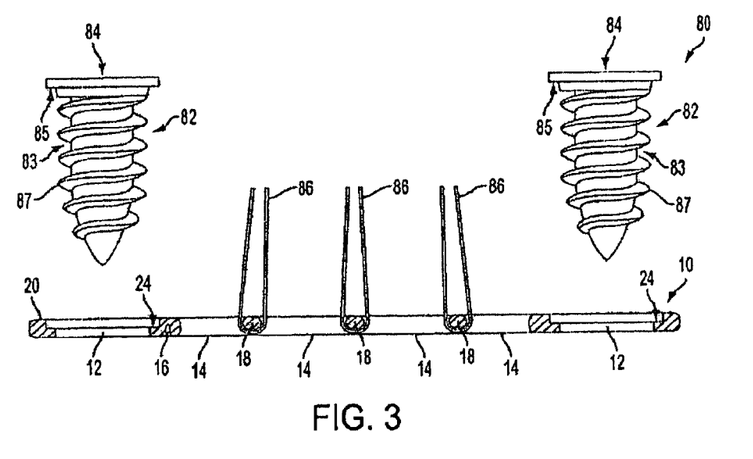
FIG. 3 is a side, cross-sectional view of the plate of FIG. 1 with a plurality of sutures coupled thereto and having a plurality of anchors positioned near openings formed through the plate.
Figure 4:
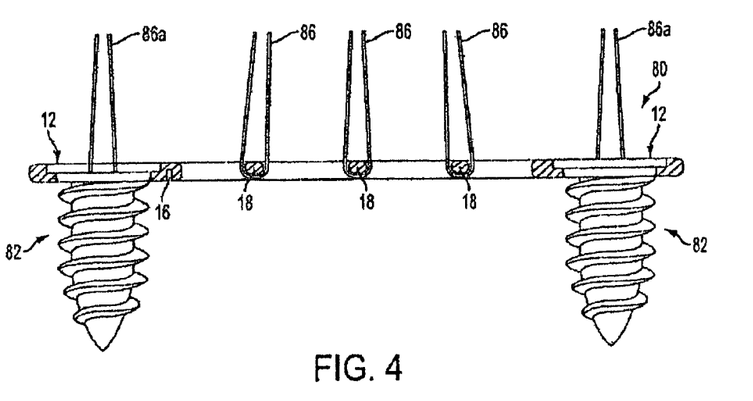
FIG. 4 is a side, cross-sectional view of the plate of FIG. 3 with the anchors seated in the anchor seating openings.

The openings 12 can each have any size and shape, the same or different from one another. In an exemplary embodiment, the openings 12 can have a same size and shape so that they can interchangeably seat identical bone fixation elements such as the identical anchors 82, shown in FIGS. 3 and 4. As shown generally in FIGS. 3 and 4, a system 80 can include the plate 10 and one or more anchors 82. Generally, the size and shape of the openings 12 can approximate a size and shape of an outer diameter of the anchors 82. The openings 12 can each be sized and shaped such that an anchor head 84 of the anchor 82 can engage the plate 10 while being at least partially recessed within the plate 10. In an exemplary embodiment, the openings 12 can each be sized and shaped such that when the anchor 82 is fully seated within the opening 12, e.g., fully distally advanced therethrough, the anchor head 84 of the anchor 82 can be seated flush or sub-flush with the tissue seating surface 20 of the plate 10, which can help prevent the anchor head 84 from digging into or otherwise damaging tissue abutting the tissue seating surface 20. The openings 12 can each be sized, shaped, and/or include a locking feature configured to secure the anchor 82 therein, such as by creating a frictional fit, interference fit, compression fit, snap fit, etc. between the anchor head 84 and the plate 10. In this way, once the plate 10 is positioned and the anchors 82 are driven into bone, the anchors 82 can be locked in place relative to the plate 10, which can help prevent inadvertent backing-out of the anchors 82 and/or inadvertent loosening of the plate 10. Additionally or alternatively, a shank 83 of each of the anchors 82 can include one or more bone engaging features 87, e.g., threads (as in the illustrated embodiment), ridges, barbs, textured gripping surface, etc., which can help prevent inadvertent backing-out of the anchor 82 from bone, as will be appreciated by a person skilled in the art. FIG. 4 illustrates the anchors 82 seated in openings 12 with the heads 84 flush with the tissue seating surface 20 of the plate 10, with the shanks 83 extending distally beyond the bone contacting surface 22 of the plate 10, and with sutures 86 a coupled thereto, e.g., by being passed around a suture engaging member located within an inner lumen thereof. Although only one suture 86 a is shown coupled to each of the anchors 82, and each of the sutures 86 a is shown as a non-folded single strand, any number of sutures can be coupled to each of the anchors 82, same or different from one another, and any of the sutures can be folded so as to be 2-ply, 3-ply, etc. Also, although anchors 82 are shown advanced through each of the openings 12, in use, anchors need not be advanced through each of the openings 12 and into bone. For non-limiting example, a plate can include a plurality of openings at each opposed end of the plate, with anchor(s) being advanced through selected ones of the anchor seating openings based on, e.g., patient anatomy.

Figure 2:
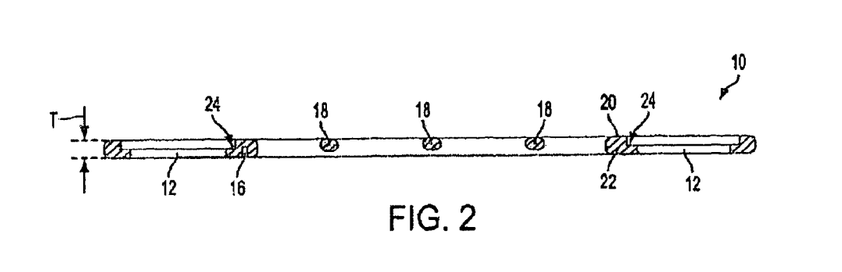
FIG. 2 is a side, cross-sectional view of the plate of FIG. 1.

The openings 12 can each include a shelf 24 configured to facilitate seating an anchor head 84 of the anchor 82 therein. As best shown in FIGS. 2 and 3, the shelves 24 can each have a size and shape that allows the anchor head 84 to be seated therein. While the shelves 24 in the illustrated embodiment have a square edge, the shelves 24 can have a continuous angled edge or a curved edge. The shelf 24 of each opening 12 can define differently sized proximal and distal portions of the opening. The proximal portion can have a larger size than the distal portion, which can mimic the anchor head 84 which includes a shelf 85 defining proximal and distal portions of the head 84 in which the proximal portion of the head 84 has a larger size than the head's distal portion. The openings need not include shelves, e.g., if anchors to be seated therein have rounded heads, such as with polyaxial anchors.

The anchors 84 shown in FIGS. 3 and 4 are non-limiting embodiments of anchors that can be used with the plate 10. Any anchor can be received in bores formed in any of the plates disclosed herein, such as, for non-limiting example, HEALIX® available from DePuy Mitek of Raynham, Mass., HEALIX PEEK® available from DePuy Mitek of Raynham, Mass., HEALIX BR® available from DePuy Mitek of Raynham, Mass., and embodiments of anchors discussed in U.S. Pat. No. 8,114,128 issued Feb. 14, 2012 entitled "Cannulated Suture Anchor" and U.S. patent application Ser. No. 11/855,670 (U.S. Pat. Pub. No. 2009/0076544) filed Sep. 14, 2007 entitled "Dual Thread Cannulated Suture Anchor," which are hereby incorporated by reference in their entireties.

Although the plate 10 is illustrated in FIG. 4 as having the anchors 82 coupled thereto, as mentioned above, one or more bone fixation elements in addition to or instead of anchors can be coupled to the plate 10 as well as to other embodiments of plates disclosed herein. As also mentioned above, the one or more bone fixation elements coupled to a plate can be integrally formed therewith or can be independent elements mateable to the plate such that the plate can include all integral bone fixation elements, can include no integral bone fixation elements, or can include a combination of integral and independent bone fixation elements. Exemplary embodiments of bone fixation elements include suture anchors, a suture bushing or eyelet configured to sliding receive a suture or other flexible securing member therethrough, a suture linelock or other unidirectional suture passage mechanism, an adhesive or cement, etc. Non-limiting embodiments of a suture bushing or eyelet are described in further detail in U.S. Pat. No. 5,860,978 issued Jan. 19, 1999 entitled "Methods And Apparatus For Preventing Migration Of Sutures Through Transosseous Tunnels," which is hereby incorporated by reference in its entirety.

Referring again to the embodiment shown in FIGS. 1-4, the plurality of additional openings 14, also referred to herein as "holes," formed in the plate 10 can each have a variety of sizes, shapes, and configurations. The plate 10 can include any number of holes 14 equal to or greater than two so as to define at least one land region 18. Because one land region can be defined by two holes, a plate can include a total number of land regions equal to one less than a total number of holes. In the exemplary embodiment illustrated in FIGS. 1-4, the plate 10 includes four holes 14 and three land regions 18.

Figure 1:
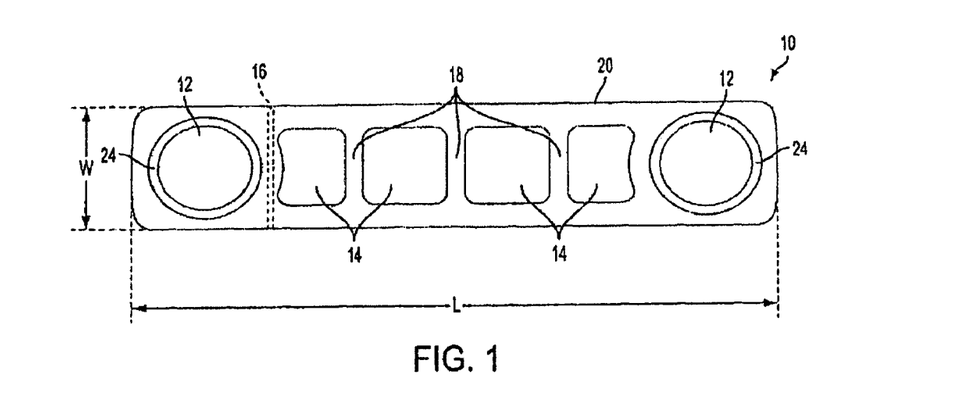
FIG. 1 is a top view of one embodiment of a tissue repair suture plate in an expanded configuration.

The holes 14 can be located anywhere along the length L of the plate 10. As in the illustrated embodiment, the holes 14 can be formed in an intermediate portion of the plate 10 positioned between the openings 12 form in the plate 12. In other words, the openings 12 can be formed in end regions of the plate 10, and the holes 14 can be bookended by the openings 12. By being located between the openings 12, suture(s) passed through the holes 14 can be less likely to interfere with insertion of bone fixation elements such as the anchors 82 through the openings 12 and into bone. The holes 14 can be equidistantly spaced from one another along the length L of the plate 10, which can help improve load balancing. The holes 14 can be longitudinally aligned with one another and with the openings 12, as best shown in FIG. 1. The holes 14 can also be centered lengthwise and/or widthwise in the plate 10, which can facilitate load balancing and/or can help prevent the plate 10 from buckling when anchor(s) are inserted therethrough. The holes 14 can generally be in the form of slots that extend at least partially across the width W of the plate 10. In an exemplary embodiment, the holes 14 can extend across a substantial amount of the width W of the plate 10 so as to maximize a length of the land regions 18 across the plate's width W, which can provide versatility of placement in passing suture(s) 86 through the holes 14 and looping the suture(s) 86 around the land regions 18, as shown in FIG. 4 and discussed further below, and which can help maximize a surface area of tissue, e.g., tissue abutting or facing the plate's tissue contacting surface 20, contacting bone abutting or facing the plate's bone contacting surface 22, which can facilitate healing.

The holes 14 can each have any size and shape, the same or different from one another. The holes 14 can each have a relatively large size relative to a size of the plate 10, which similar to that mentioned above, can help maximize the surface area of tissue contacting bone. As in the illustrated embodiment, the holes 14 immediately adjacent to the openings 12, e.g., outermost ones of the holes 14, can have a different shape than the other holes 14. This different shape can reflect the shape of the openings 12 so as to help maximize the size of the holes 14 while providing an adequate thickness between the openings 12 and the holes 14 to help maintain structural integrity of the plate 10.

As mentioned above, the land regions 18 can be located between adjacent ones of the holes 14 and can each be configured to engage one or more sutures 86, also referred to herein as "strands of suture" or "suture strands," passed through the adjacent holes 14 defining the land region 18. In other words, the land regions 18 can be configured as suture engaging members configured to receive at least one suture 86 therearound such that limbs or trailing ends of the suture(s) 86 can extend through different one of the holes 14. The land regions 18 can therefore provide a surface for one or more of the suture strands 86 to abut against, which can facilitate pulling tissue coupled to the suture(s) into contact with the plate 10.

The land regions 18 can have a variety of sizes, shapes, and configurations, the same or different from one another. The land regions 18 in the embodiment shown in FIGS. 1-4 are identical to one another. As in the illustrated embodiment, the land regions 18 can include generally elongate bars or rods having a substantially uniform, oval cross sectional shape, although the cross sectional shape of the land regions 18 can vary along lengths thereof. For non-limiting example, portions of the land regions 18 can have one or more sutureabutting regions that can have a curved or circular cross sectional shape, and one or more non-suture abutting regions that can have a different cross sectional shape, e.g., a rectangular shape. In addition, the suture-abutting portions can be recessed in the land regions 18 to help maintain different suture strands at different locations along the length of the land regions 18. The ovular cross sectional shape of the land regions 18 can provide a relatively smooth surface for the suture strands 86 to abut against, which can reduce the likelihood of the sutures 86 fraying as they abut and/or are slid against the land regions 18. In another embodiment, the cross sectional shape of the land regions 18 can be non-oval, e.g., a semicircular or crescent-shaped where a bottom or distal portion of the land region can be curved while a top portion can be flat, rectangular, triangular, irregularly shaped, etc.

One or more sutures 86 can be slidably disposed around land regions 18 by being passed through adjacent openings 14. The suture(s) 86 can each be coupled to tissue (not shown) to help secure the tissue to the plate 10 and to bone underlying the plate 10. The suture(s) 86 can therefore allow the tissue to be secured to the bone without an anchor or other fixation element connected to the suture(s) 86 being inserted into the bone, which can help prevent damaging the bone, as mentioned herein. While only one suture 86 is shown coupled to each land region 18, any number of sutures 86 can be coupled to each land region 18, the same or different from one another. Although each of the sutures 86 is shown as a non-folded single strand, any of the sutures can be folded so as to be 2-ply, 3-ply, etc. The sutures 86 can each be coupled to a single land region 18, as shown in FIGS. 3 and 4, or any of the sutures 86 can make more than two passes through the holes 14, e.g., to weave sutures 86 through more than two of the holes 14 to create additional frictional engagement with the land regions 18. The sutures 86 can slidably engage the land regions 18, as also shown in FIGS. 3 and 4, such that the sutures 86 can freely slide therearound, at least until a tissue is coupled to the sutures 86 and the plate 10 is attached to bone. Alternatively, any of the sutures 86 can be tied or knotted to any of the land regions 18, which can help prevent tissue movement relative to the plate 10 and underlying bone when the plate 10 is attached to the bone. Although each of the land regions 18 has a suture 86 coupled thereto in the illustrated embodiment, one or more of the land regions 18 may not have a suture coupled thereto based on, e.g., a size of a tissue coupled to the plate 10.

In an exemplary embodiment, each of the sutures 86 coupled to the land regions 18 can be preloaded, e.g., coupled to the plate 10 before the plate 10 is introduced into a patient's body. The sutures 86 can be preloaded by a surgeon or other user associated with a surgical procedure in which the plate 10 is to be used, or the plate 10 can be provided as a sold unit to surgeon or other user associated with a surgical procedure with the sutures 86 already coupled thereto. Providing the plate 10 with the sutures 86 coupled thereto as a sold unit can help save surgical time.

As mentioned above and as shown in FIG. 4, in addition to coupling the one or more sutures 86 to the land regions 18, one or more sutures 86a can also be coupled to one or more of the anchors 82 (or other bone fixation elements) seated in the openings 12, which can provide additional tissue fixation points for tissue coupled to the sutures 86 and help distribute the load along the tissue when the plate 10, and hence the tissue coupled thereto, is secured against bone.

The plate 10 can, as mentioned above, optionally be configured to be movable between folded and expanded configurations. Being so movable can facilitate introduction of the plate 10 into a patient's body through a tissue opening having diameter that is less than the length L of the plate 10, e.g., less than an implanted size of the plate 10. The plate 10 can be biased to the expanded configuration such that an external force is required to maintain the plate 10 in the folded configuration, which can help prevent the plate 10 from folding after implantation in a patient's body and consequently moving tissue out of contact with underlying bone. In embodiments where a plate is substantially flexible, e.g., when the plate is formed from a flexible material such as a mesh material, the plate in the folded configuration can be folded any number of times along any number of portions thereof. A flexible plate can, however, include one or more predetermined folding regions, which can facilitate folding of the plate in predictable area(s) that may be less likely to cause any damage to the plate and/or interfere with any sutures coupled thereto. In embodiments where a plate is substantially rigid, the plate can have one or more predetermined folding regions, same or different from one another, configured to allow folding of the plate. The predetermined folding regions can have a variety of configurations. Non-limiting examples of a predetermined folding region includes a weakened region of the plate, a scored region of the plate, a region of the plate formed from a flexible material, and a hinge, e.g., a living hinge.

As mentioned above, the plate 10 shown in FIGS. 1-4 includes a hinge 16, which can be configured as a predetermined folding region at which the plate 10 can be folded to thereby be in a folded configuration. The plate 10 is shown in an expanded configuration in FIGS. 1-4, with the length L of the plate 10 defining a maximum length of the plate 10 in the expanded configuration and with the width W of the plate 10 defining a maximum width of the plate 10 in the expanded configuration. When the plate 10 is in the folded configuration, the plate's maximum length and/or maximum width can be respectively less than the maximum length and/or maximum width of the plate 10 in the expanded configuration, which can facilitate introduction of the plate 10 into a body of a patient through a relatively small tissue opening.

The hinge 16 can be located anywhere along the length L of the plate 10, such as in the intermediate region of the plate 10 between the openings 12. The plate 10 can therefore be folded at a location between the openings 12. The hinge 16 can be located in the intermediate region immediately adjacent to a one of the openings 12 such that all of the holes 14 are located on one side of the hinge 16, which can minimize a size of plate 10 in the folded configuration and facilitate minimally invasive introduction of the plate 10 into a patient's body.

The hinge 16 can have a variety of sizes, shapes, and configurations. In an exemplary embodiment, the hinge 16 can include a living hinge, e.g., a thinned region of the plate 10 formed from a same material(s) as a remainder of the plate 10. The hinge 16 as a living hinge, as in the embodiment illustrated in FIGS. 1-4, can ease manufacturing the plate 10, such as by injection molding. The hinge 16 can have any number of other configurations, as will be appreciated by a person skilled in the art, such as a barrel hinge. The hinge 16 can extend lengthwise (e.g., substantially parallel to a longitudinal axis of the plate 10), widthwise (e.g., substantially perpendicular to the longitudinal axis of the plate 10), or at another angle along the plate 10 (e.g., intersecting the longitudinal axis of the plate 10 at a non-zero and non-90-degree angle). The hinge 16 can extend widthwise along the entire width W of the plate 10, as in the illustrated embodiment. Although the plate 10 only includes one hinge 16, the plate 10 can include at least one additional hinge, such an additional hinge adjacent the opening 12 at the end of the plate 10 opposed to the end that includes the illustrated hinge 16.

As mentioned above, the plate 10 shown in FIGS. 1-4 has a constant width W along the length L of the plate 10, but a plate can have a non-varying width along a length thereof. In an exemplary embodiment, a plate having a non-varying width can be wider at opposed ends thereof than in an intermediate portion of the plate extending between the opposed ends. The plate can therefore be configured to be coupled to bone fixation element(s) at at least one of the opposed ends thereof, either by coupling to independent bone fixation element(s) or having bone fixation element(s) integrally formed therewith, while minimizing an amount of the plate between the opposed ends thereof that contact underlying bone so as to maximize an amount of tissue coupled to the plate in contact with the bone, which can facilitate healing.

Figure 5:
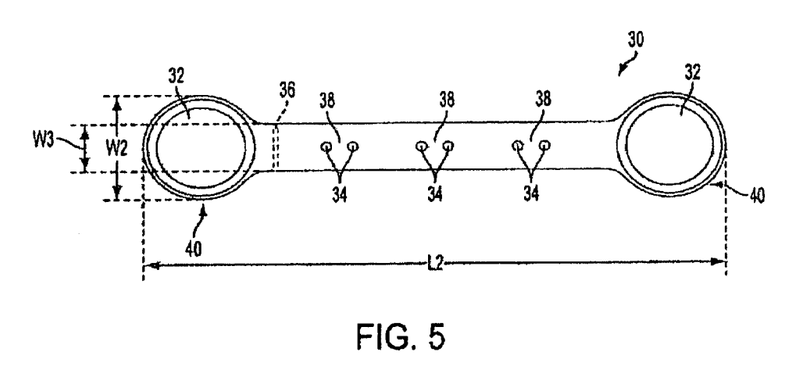
FIG. 5 is a top view of another embodiment of a tissue repair suture plate in an expanded configuration.

FIG. 5 illustrates an embodiment of a plate 30 having a non-varying width along a length L2 thereof. The plate 30 can generally be configured and used similar to other plates disclosed herein with like-named elements, e.g., openings 32, holes 34, land regions 38, and a hinge 36, configured and used similar to others discussed herein. The holes 34 in this illustrated embodiment each have substantially circular shapes and are arranged in the plate 10 in pairs, e.g., three pairs of two holes. The plate 30 of FIG. 5 has a dogbone shape such that the plate 10 has a varying width along the length L2 thereof. A plate can have a varying width along a length thereof while having another shape, such as an ovular shape or an hourglass shape. As mentioned above, having a varying width can help minimize a surface area of the plate 30 in contact with bone underlying the plate 10 and maximize a surface area of tissue coupled to the plate 10 in contact with the bone. In the illustrated embodiment, the plate 30 has a first width W2 at opposed ends 40 thereof in which the openings 32 are formed through the plate 30, and the plate 30 has a second, smaller width W3 in an intermediate portion of the plate 30 extending between the opposed ends 40. The first width W2 can be the same at both of the opposed ends 40. The second width W3 can be substantially constant as in the illustrated embodiment. In the illustrated embodiment the second width W3 of the intermediate portion is approximately half the first width W2 of the opposed ends 40, but the first and second widths W2, W3 can have any ratio, and, as mentioned above, the first and second width W2, W3 can be different from each other in different parts of the plate 10.

While a single intermediate portion is shown in the embodiments of FIGS. 1-5, in another embodiment, a plate can include multiple, narrower intermediate portions, and each intermediate portion can have at least one hole formed therethrough. For example, a plurality of intermediate portions can be disposed substantially parallel to one another between opposed ends of the plate. In addition, or instead of, holes formed through the intermediate region of the plate, additional land regions can extend transverse to the multiple intermediate regions resulting in a grid of land regions where one or more suture strands can be coupled. In general, increasing the number of locations where suture strands can be coupled to the surface of the plate can provide greater flexibility of suture placement and/or tissue tensioning during surgery and can allows greater distribution of load along the tissue.

A plate can optionally include one or more bone engaging surface features configured to engage bone underlying a bone contacting surface of the plate. The one or more bone engaging surface features can facilitate secure attachment of the plate to the bone, can help minimize movement of the plate relative to the bone after implantation within a patient's body, and/or can help stabilize the plate relative to the bone prior to anchor(s) coupled to the plate being fully inserted into the bone. The bone engaging surface features can have a variety of sizes, shapes, and configurations. Generally, the bone engaging surface features can be formed on and/or extend away from the plate's bone contacting surface. Non-limiting examples of bone engaging surface features include a protrusion, a textured surface, a pin, and a tacky surface. A plate can include any number of bone engaging surface features and can include the bone engaging surface features at any location(s) along the plate. Bone engaging surface features can be integrally formed with the plate, such as by molding the bone engaging features with the plate, or the bone engaging surface features can be affixed to the plate in any number of ways, such as interference fit, snap fit, welded, adhered with glue and/or other adhesive, etc.

Figure 6:
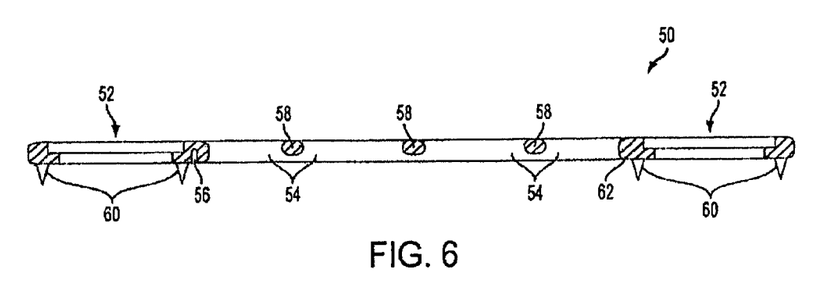
FIG. 6 is a side, cross-sectional view of another embodiment of a tissue repair suture plate in an expanded configuration.

FIG. 6 illustrates an embodiment of a plate 50 that includes one or more bone engaging surface features 60 extending from a bone contacting surface 62 of the plate 50. The plate 50 can generally be configured and used similar to other plates disclosed herein with like-named elements, e.g., openings 52, holes 54, land regions 58, and a hinge 56, configured and used similar to others discussed herein. The plate 50 includes four bone engaging surface features 60, but as mentioned above, the plate 60 can include any number of bone engaging surface features 60. In an exemplary embodiment, the bone engaging surface features 60 can be positioned adjacent the openings 52, which can help prevent the bone engaging surface features 60 from interfering with suture(s) (not shown) passed through any of the holes 54. In the illustrated embodiment, bone engaging features 60 are in the form of sharp, pointed protrusions extending from a bone contacting surface 62 of the plate that are configured to penetrate into bone.

A plate can be configured to be mated to one or more bone fixation elements, such as with the plates illustrated in FIGS. 1-5. In other words, the plate and the one or more bone fixation elements can be independent elements. A plate can, however, be integrally formed with one or more bone fixation elements such that the bone fixation element(s) need not be independently mated to the plate. A plate with integral bone fixation elements can help save time during a surgical procedure because independent bone fixation element(s) need not be aligned with plate openings and advanced therethrough into bone and because each independent bone fixation element need not be advanced separately, e.g., sequentially, into bone. A plate with integral bone fixation elements can generally be easier to implant in an open surgical procedure than in a minimally invasive surgical procedure because the plate's bone fixation element can be more easily all advanced into bone at once. If a plate is configured to seat independent bone fixation elements, the plate can be provided as part of a kit including one or more bone fixation elements configured to be seated in openings of the plate. The kit can also include one or more additional plates configured to seat one or more of the bone fixation elements included in the kit. Each of the plates included in a kit can be different from one another in one or more ways, e.g., in size, in shape, in flexibility, etc. Each of the bone fixation elements included in a kit can be identical to one another, or any one or more of the bone fixation elements can vary from other bone fixation elements included in the kit in any one or more ways A plate and bone fixation element(s) can be selected as appropriate from the kit for use in a particular surgical procedure based on, e.g., patient anatomy, type of tissue being attached to bone, etc.

Figure 7:
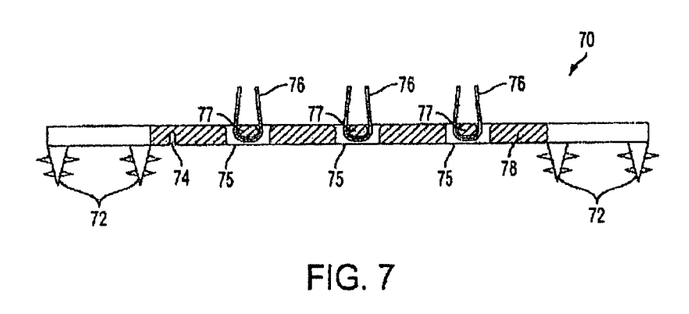
FIG. 7 is a side, cross-sectional view of another embodiment of a tissue repair suture plate in an expanded configuration and having anchors integrally formed therewith.

FIG. 7 illustrates an embodiment of a plate 70 that does not include openings but that does include one or more bone fixation elements in the form of anchors 72 integrally coupled thereto such that the plate 70 and the anchors 72 form a unitary element. The plate 70 can generally be configured and used similar to other plates disclosed herein with like-named elements, e.g., holes 75, suture 76, land regions 77, and a hinge 74, configured and used similar to others discussed herein. The plate 70 includes four integral anchors 72 coupled thereto, but a plate can include any number of integral bone fixation elements coupled thereto. In an exemplary embodiment, the integral anchors 72 can be positioned similar to the positioning discussed above regarding a plate's openings, such as adjacent opposed ends of the plate 70. In the illustrated embodiment, each of the integral anchors 72 is in the form of a sharp, pointed protrusion extending from a bone contacting surface 78 of the plate 70 and having a plurality of bone engaging features in the form of ridges. The integral anchors 72 can be integrally formed with the plate 70 in any number of ways, such as by molding the anchors 72 with the plate 70, welding thereto, snap fit, compression fit, adhered with glue and/or other adhesive, etc.

The plates discussed herein can be used in attaching tissue to bone in a variety of surgical procedures, such as a procedure for attaching tissue to bone, e.g., anterior cruciate ligament (ACL) repair, rotator cuff repair, etc. In an exemplary embodiment, a procedure including implantation of the plate can be a minimally invasive procedure, but as will be appreciated by a person skilled in the art, the plates discussed herein also have application in open surgical instrumentation as well as application in robotic-assisted surgery.

FIGS. 8-11 illustrate an exemplary embodiment of securing soft tissue to bone including implanting a plate adjacent bone to allow a soft tissue coupled to the plate via one or more sutures to contact the bone to attach the tissue thereto. While FIGS. 8-11 show securing soft tissue to bone in a rotator cuff repair, the methods and devices disclosed herein can be used at a variety of anatomical locations and in a variety of medical procedures in which tissue is attached to bone, as mentioned above. Additionally, although FIGS. 8-11 are discussed with reference to the plate 30 of FIG. 5 and the anchor 82 of FIGS. 3 and 4, any of plates and any of the bone fixation elements discussed herein can be implanted in this or other ways.

Figure 8:
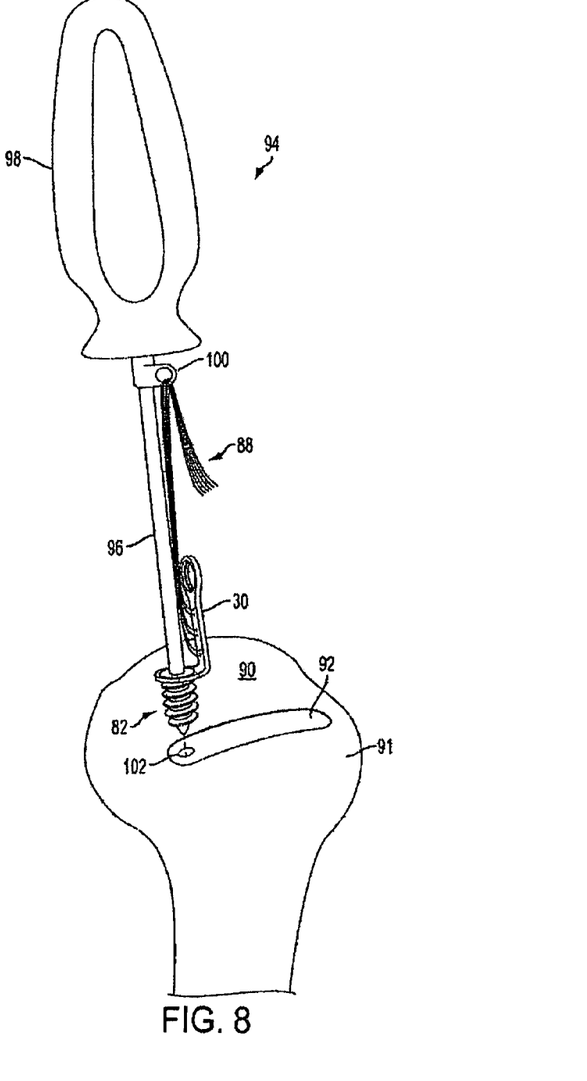
FIG. 8 is a perspective view of an embodiment of a delivery device coupled to an embodiment of an anchor disposed within an anchor seating opening formed through the plate of FIG. 5, which is in a folded configuration, the plate and the anchor being positioned adjacent a bone.
Figure 10:
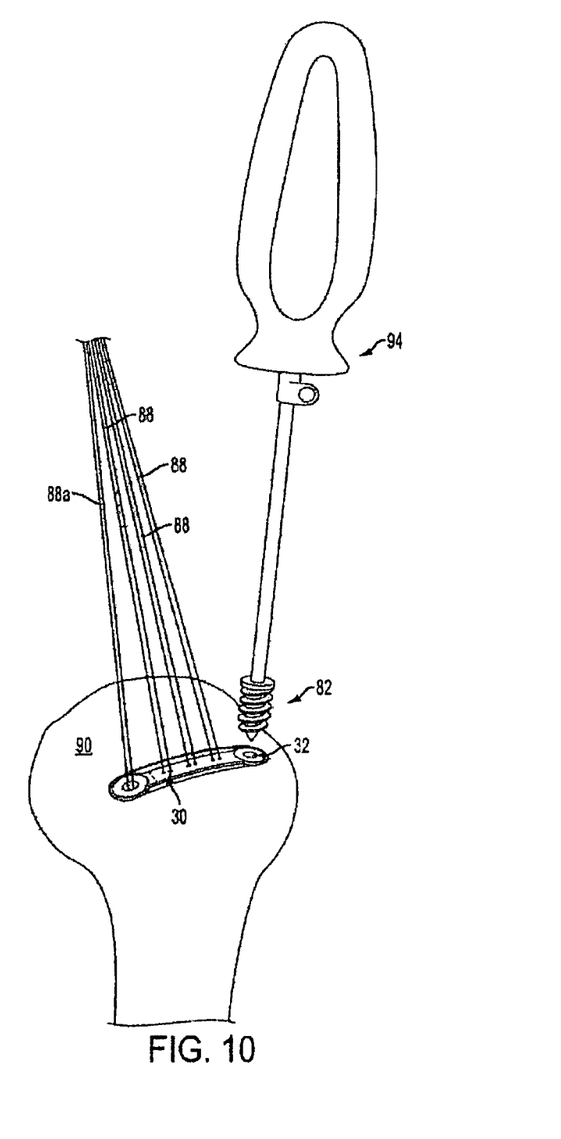
FIG. 10 is a perspective view of the delivery device of FIG. 8 and the plate, the anchor, and the bone surface of FIG. 9 with the delivery device coupled to another anchor positioned adjacent the plate.

The surgical procedure can include preparing the patient for surgery using standard techniques. In a minimally invasive procedure, one or more introducer devices (not shown), e.g., a cannula, a trocar, etc., can be advanced through an opening in the patient to provide access to a surgical site. The plate 30 can be introduced into a patient through such an introducer device, or advanced directly into the patient. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. Although a cannula can be positioned in an incision and the plate 30 and a delivery device 94 configured to deliver the plate 30 to a surgical site can be inserted therethrough, for clarity, FIGS. 8 and 10 show the delivery device 94 without an introducer device therearound.

The delivery device 94 can have a variety of sizes, shapes, and configurations. Although the delivery device 94 is shown in FIGS. 8 and 10 as delivering the plate 30 to the surgical site, any number of other delivery devices can be used to deliver the plate 30 to the surgical site. As in the illustrated embodiment, the delivery device 94 can include a shaft 96 having a handle portion 98 at a proximal end thereof the shaft 96 and a mating portion (obscured in FIGS. 8 and 10) at a distal end of the shaft 96 configured to mate to a proximal end of an anchor, such as the anchor 82 or an anchor integrally formed with a plate. The delivery device 94 can include at least one suture engaging feature 100 configured to engage one or more sutures, e.g., the sutures 86 pre-fed through the holes 34 formed through the plate 30. The at least one suture engaging feature 100 can be located anywhere on the delivery device 94, but in an exemplary embodiment, the at least one suture engaging feature 100 can be located in a proximal portion thereof, e.g., at the proximal end of the shaft 96, which can allow the sutures engaging the at least one suture engaging feature 100 to extend outside the patient's body for manipulation, as the shaft's proximal end can remain outside the patient's body throughout the surgical procedure. The at least one suture engaging feature 100 can have a variety of sizes, shapes, and configurations, such as an eyehole (as in the illustrated embodiment), a clamp, a clip, a groove formed in the delivery device 94, a spool, etc. The eyehole's opening in the illustrated embodiment is circular and is substantially perpendicular to a longitudinal axis of the shaft 96 of the delivery device 94, but an eyehole's opening can have any shape and can be at any orientation relative to the shaft's longitudinal axis.

Figure 12:
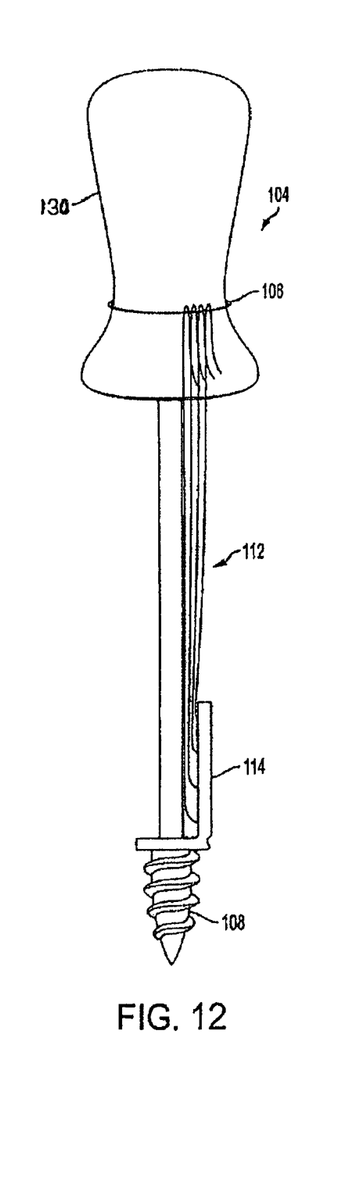
FIG. 12 is a side view of another embodiment of a delivery device, the delivery device being coupled to another embodiment of an anchor disposed within an anchor seating opening formed through another embodiment of a tissue repair suture plate.

FIG. 12 illustrates another embodiment of a delivery device 104 that includes a suture engaging feature 106 in the form of an o-ring extending around an external perimeter of a handle 130 of the delivery device 104. FIG. 12 also shows a distal end of the delivery device 104 coupled to an anchor 108 mated to a plate 114 and shows a plurality of sutures 112 coupled to the suture engaging feature 106, extending longitudinally along the delivery device 104, and coupled to the plate 114. The plate 114 can be generally configured and used similar to other plates disclosed herein.

Referring again to the embodiment of FIGS. 8-11, prior to delivery of the plate 30, a bone surface 90 of a bone 91 to which the plate 30 is to be attached can be prepared, as will be appreciated by a person skilled in the art. For non-limiting example, one or more bores 102 can be formed in the bone surface 90 to respectively receive the anchors 82 therein, and the bone surface 90 where the plate 30 is to be affixed can be decorticated prior to affixing the plate 30 thereto, which can help position the plate 30 flush with the bone surface 90. The bore 102 can be sized to fully receive the anchor 82 therein, or the bore 102 can be a starter bore that is smaller than the anchor 82, with the anchor 82 being configured to penetrate into bone as necessary to fit the anchor 82 therein. A diameter of the bore 102 can be slightly less than a maximum outer diameter of the anchor 82, and a length of the bore 102 can be substantially equal to or greater than a length of the anchor 82. The bore 102 can extend fully through cortical bone to allow the anchor 82 to be fully engaged through the thickness of the cortical bone. A single bore 102 is shown as being initially formed in FIG. 8, but multiple initial bores 102 can be formed, e.g., for each of the anchors 82 already coupled or to be coupled to the plate 30, prior to any of the anchors 82 being advanced into the bone 91. In an exemplary embodiment, the bores 102 can be first formed for anchor(s) at one opposed end of the plate 30 and formed for anchor(s) at one opposed end of the plate 30 after the anchor(s) are advanced into the first bore(s) 102 to help ensure that the additional bores 102 properly align with the additional anchors.

As shown in FIG. 8, the delivery device 84 can deliver the plate 30 in a folded configuration adjacent to the bone surface 90 at a tissue attachment site 92. The plate 30 can be coupled to the distal end of the delivery device 94 outside the patient's body, and then the distal end of the delivery device 94 with the plate 30 coupled thereto can be advanced into the patient's body, such as through an introducer device as discussed above. The plate 30 can be coupled to the delivery device 94 in a variety of ways. In an exemplary embodiment, the anchor 82 can be advanced into the opening 32 formed through the plate 30, and the delivery device's distal end can be coupled to the anchor 82, such as by being advanced through a proximal end of the anchor 82 and into an inner lumen of the anchor 82. The delivery device's distal end can be coupled to the anchor 82 before or after the anchor 82 is advanced into the opening 32. In an exemplary embodiment, the anchor 82 to which the delivery device 94 is coupled during delivery of the plate 30 in the folded configuration to the site 92 is seated in the opening 32 adjacent to the hinge 36, which can minimize the plate's footprint in the folded configuration, which, as mentioned above, can allow the plate 30 to be advanced into a patient's body through a relatively small opening, such as an incision.

One or more sutures 88 attached to the plate 30 can engage the suture engaging feature 100 of the delivery device 94 prior to the plate 30 being advanced into the patient's body. The one or more sutures 88 can be attached to the plate 30 by passing through the holes 34 and engaging the land regions 38. The sutures 88 can be attached to the plate 30 before the delivery device 94 is coupled to the plate 30, such as by the sutures 88 being pre-fed through the holes 34. Although a single strand of suture 88 is passed through each of the holes 34 such that each of the holes 34 has one suture 88 extending therethrough and such that each of the land regions 38 has one suture engaged therewith, as mentioned above, any number of sutures can be passed through any one or more of the holes 34 and can be folded any number of times. Additionally, the sutures 88 in the illustrated embodiment are slidably coupled to the plate 30, but the sutures 88 can be non-slidably coupled thereto, e.g., by tying the sutures 88 to one or more of the land regions 38 or weaving or making multiple passes through the holes 34 to provide additional frictional engagement with the plate 30.

The plate 30 can be coupled to the delivery device 94 in an expanded configuration, and the introducer device (not shown), e.g., a cannulated channel thereof, can apply an external force to the plate 30 to move the plate 30 from the expanded configuration to the folded configuration, e.g., to bend the plate 30 at the hinge 36, and hold the plate 30 in the folded configuration during delivery to the tissue attachment site. Additionally or alternatively, a distal pulling force can be applied to suture(s) 88 coupled to the plate 30 to apply an external force to the plate 30 to move the plate 30 from the expanded configuration to the folded configuration, and hold the plate 30 in the folded configuration during delivery to the tissue attachment site, regardless of whether the plate 30 is fully or partially disposed within an introducer device.

Thus, as shown in FIG. 8, the plate 30 can be delivered to the tissue attachment site 92 in the folded configuration with different regions of a tissue seating surface of the plate 30 moved toward one another, with the intermediate portion of the plate 30 and one opposed end of the plate 30 (e.g., the opposed end which does not have the anchor 82 seated therein to which the delivery device 94 is coupled) extending along the delivery device's shaft 96, with the anchor 82 positioned within one of the openings 32, with the sutures 88 passing through the holes 34 and around the land regions 38, and with the sutures 88 extending from the plate 30 along the shaft 96 to the suture engaging feature 100. If a plate has more than one hinge, the plate can be bent at any one or more of the hinges during delivery into a patient's body.

Once the plate 30 and the anchor 82 are positioned at the tissue attachment site 92, the delivery device 94 can drive the anchor 82 at least partially into the bore 102 (or into the bone 91 directly if the bore 102 is not pre-formed in the bone 91) to affix a first end of the plate 30 to the bone 91. As in the illustrated embodiment, the anchor 82 and the opening 32 can be sized to allow relative rotational motion therebetween so the orientation of the plate 30 is not disrupted when the anchor 82 is driven into the bone 91. When the anchor 82 is being driven into the bone 91, the other opposed end of the plate 30, e.g., the end extending along the shaft 96 of the delivery device 94, and/or at least a portion of the plate's intermediate portion can remain disposed within the introducer device (if used). The plate 30 can therefore remain in the folded configuration when the anchor 82 is driven into the bone 91, and the sutures 88 can extend proximally away from the anchor 82, thereby helping to prevent snagging the anchor 82 on any of the sutures 88, which could damage the anchor 82 and/or the sutures 88. Because the anchor 82 can be advanced through the opening 32, which can have a diameter larger than a maximum diameter of the anchor 82, the anchor 82 can be driven into the bone 91 without disrupting the orientation of the plate 30 relative to the bone 91 when the anchor 82 is driven into the bone 91. In other words, the anchor 82 can be rotated to threadably advance into the bone 91 without rotating the plate 30.

The anchor 82 can be fully or partially advanced into the bone 91 before the anchor 82 at the other opposed end of the plate 30 is driven into the bone 91 and/or before the plate 30 moves from the folded configuration to the expanded configuration. In an exemplary embodiment, the anchor 82 can be partially driven into the bone 91, and the plate 30 can then be rotated and/or otherwise repositioned relative to the anchor 82 to optimally positioned the plate 30 relative to the bone 30, e.g., to align the plate 30 with a decorticated area of the bone 91.

In another embodiment using one or more bone fixation elements other than anchors, such as a suture line-lock or a suture bushing or eyelet, a plate can be attached to bone by positioning one or more openings formed through the plate above respective tunnel(s) prepared through the bone, and passing and securing suture through the opening(s) and the tunnel(s). Non-limiting embodiments of using a suture bushing or eyelet to attach suture to bone are described in further detail in previously-mentioned U.S. Pat. No. 5,860,978 issued Jan. 19, 1999 entitled "Methods And Apparatus For Preventing Migration Of Sutures Through Transosseous Tunnels."

Figure 9:
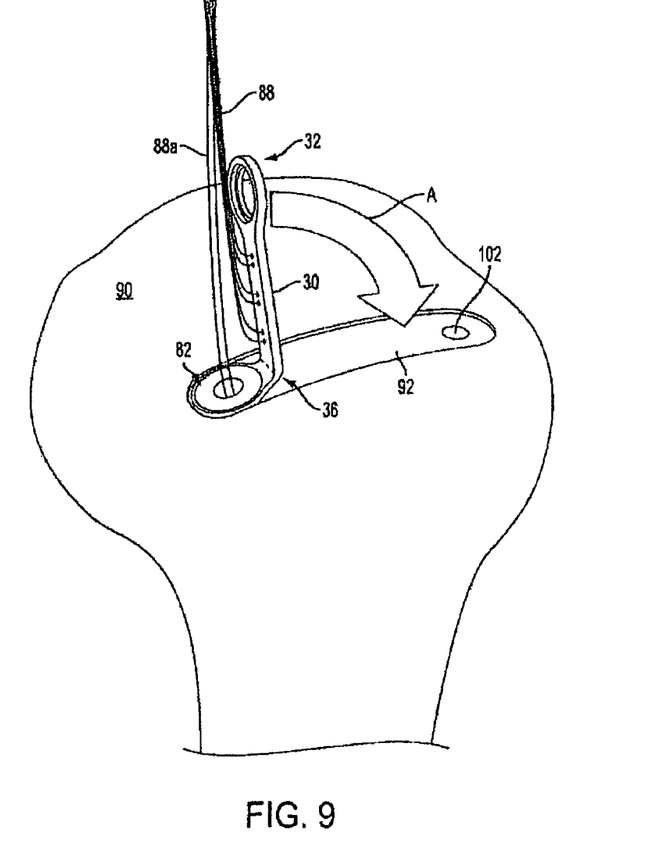
FIG. 9 is a perspective view of the plate, the anchor, and the bone of FIG. 8 with the anchor advanced into the bone, the delivery device having been removed from the anchor.

Referring again to the embodiment of FIGS. 8-11, as shown in FIG. 9, at least one additional suture 88*a* can be coupled to the anchor 82. The at least one additional suture 88*a* can be coupled to the anchor 82 before or after the anchor 82 is advanced into the bone 91 and before or after the plate 30 moves from the folded configuration to the expanded configuration. The at least one additional suture 88*a* can be coupled to the suture engaging feature 100 of the delivery device 94 similar to that discussed above regarding the sutures 88.

As also shown in FIG. 9, after the anchor 82 has been driven into the bone 91, the plate 30 can be moved from the folded configuration to the expanded configuration, e.g., by bending the plate 30 at the hinge 36 in the direction A, to position the other opposed end adjacent to the bone 91. If the sutures 88 were not coupled to the plate 30 prior to delivery of the plate 30 to the tissue attachment site 92, the sutures 88 can be coupled to the plate 30 prior to or during movement of the plate 30 to the expanded configuration. Another anchor 82 can be advanced through the other opening 32 formed through the plate 30 and into the bone 91, as shown in FIG. 10. As mentioned above, another bore 102 can be formed at a location where the other anchor 82 will be advanced into the bone 91, and the other anchor 82 can be advanced into the other bore 102. Before the other bore 102 is formed, the plate 30 can be unfolded to move from the folded configuration to the expanded configuration to ensure proper alignment between the opening 32 and the other bore 102, e.g., the bore 102 can be formed by drilling through the opening 32. The other anchor 82 can be advanced into the bone 91 in a variety of ways. In an exemplary embodiment, after the anchor 82 is advanced at least partially into the bone 91, the delivery device 94 can be uncoupled therefrom, e.g., removed from the anchor's inner lumen, and can be coupled to the other anchor 82, by inserting the delivery device's distal end into an inner lumen of the other anchor 82. The delivery device 94 can then drive the other anchor 82 into the bone 91 similar to the delivery device's driving on the anchor 82 into the bone 91. Similar to that mentioned above, the other anchor 82 can be advances into the bone 91 without disrupting the orientation of the plate 30 relative to the bone 91. The sutures 88 can be disengaged from the delivery device 94 prior to driving the other anchor 82 into the bone 91, as shown in FIG. 10, which can help prevent the sutures 88 from snagging on the other anchor 88 and/or tangling on the delivery device's shaft 94. Whether engaged with or disengaged from the delivery device 94 prior to driving the other anchor 82 into the bone 91, the sutures 88 and the additional suture 88a can be tensioned to keep the sutures 88 and the additional suture 88a substantially taught, as shown in FIG. 10, which can help prevent the sutures 88 from snagging on the other anchor 88 and/or tangling on the delivery device's shaft 94.

At least one additional suture (not shown) can be coupled to the other anchor 82, similar to the at least one additional suture 88a discussed above regarding the anchor 82. The at least one additional suture can be coupled to the other anchor 82 before or after the other anchor 82 is advanced into the bone 91 and before or after the plate 30 moves from the folded configuration to the expanded configuration. The at least one additional suture can be coupled to the suture engaging feature 100 of the delivery device 94 similar to that discussed above regarding the sutures 88.

After the second anchor 82 is at least partially driven into the bone 91, each of the anchors 82 advanced through the plate's openings 32 can be fully driven into the bone 91, if not already so fully driven, so as to seat the anchors' heads into the anchor seating openings 32. As discussed above, one or both of the openings 32 can include a locking feature configured to secure the anchors 82 therein.

Figure 11:
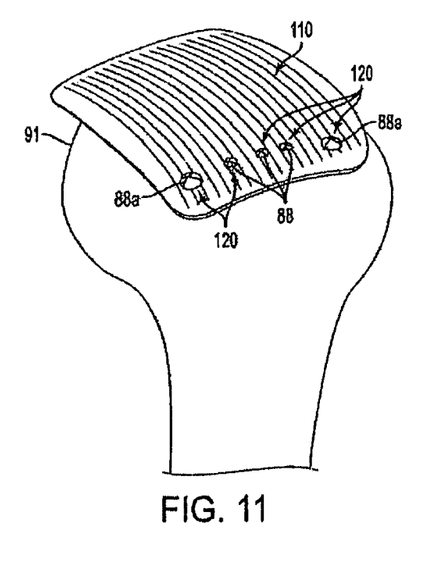
FIG. 11 is a perspective view of a tissue attached to the bone of FIG. 10.

After the plate 30 is affixed to the bone 91, the sutures 88 are coupled to the plate 30, and the additional sutures 88a are coupled to the anchors 82, a tissue 110 can be attached to the plate 30 and the bone 91 via the sutures 88, 88a, as shown in FIG. 11. The tissue 110 can be attached to the sutures 88, 88a in any order and at any time during attachment of the tissue 110 to the bone 91. In an exemplary embodiment, the tissue 110 can be attached to each of the sutures 88, 88a after the plate 30 has been attached to the bone 30 by fully advancing the anchors 82 into the bone 91. Each of the sutures 88, 88a can be passed through one of a plurality of fixation points 120 in the tissue 110 that can each be substantially directly above the location where each of the sutures 88, 88a is coupled to the plate 30 or the anchors 82.

The tissue 110 can be advanced to the bone surface 90 in any number of ways as will be appreciated by a person skilled in the art, such as by pulling and positioning the tissue 110 into proximity of the plate 30 until a surface of the tissue 110 abuts a tissue seating surface of the plate 30. Advancing the tissue 110 into contact with the tissue seating surface of the plate 30 in a distal direction can facilitate a smooth interface between a surface of the tissue 110 and the plate 30 and help avoid pulling the tissue 110 in a transverse direction which can cause the tissue 110 to pucker or fold, which can have an adverse impact on the integrity of the tissue attachment. After the tissue 110 is pulled into contact with the tissue seating surface of the plate 30, the tissue 110 can be secured to the plate 30 in any way, such as by tying or by knotting. The tissue 110 can thus be secured to the plate 30 and the bone surface 90 at a plurality of fixation points 120 located along the surface of the tissue 110. The greater a number of fixation points, the more the load on the tissue 110 at any one point can be reduced, thereby increasing the likelihood that the tissue 110 will successfully re-attach to the bone 91 in a timely manner and not tear away from any of the fixation points 120.

The various methods and devices disclosed herein can be used in a variety of surgical procedures, however the methods and devices are particularly useful for repairing a torn rotator cuff in a human shoulder.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    affixing an elongate plate to bone in proximity to detached soft tissue using one or more bone fixation elements extending into the bone, the one or more bone fixations elements each having a head engaging the plate, the plate having a plurality of openings, and a plurality of suture strands extending from the plate along a length thereof, each of the plurality of openings having at least one of the plurality of suture strands extending therethrough;
    passing the suture strands through portions of the detached soft tissue and drawing the detached soft tissue into contact with the plate and the bone; and
    securing the soft tissue with the suture strands at a desired position in contact with the plate and the bone.

2. The method of claim 1, wherein the soft tissue is secured to the plate and bone by at least one of knotting and tying one or more of the suture strands.

3. The method of claim 1, wherein one or more of the suture strands are secured to the one or more bone fixation elements.

4. The method of claim 1, wherein the suture strands are attached to and extend from the elongate plate before affixing the elongate plate to bone.

5. The method of claim 1, wherein the suture strands are attached to the elongate plate after delivering the elongate plate into a body of a patient including the bone to which the elongate plate is affixed.

6. The method of claim 1, further comprising delivering the elongate plate into a body of a patient to a tissue reattachment site in a delivery configuration in which the plate is folded.

7. The method of claim 6, further comprising, prior to affixing the elongate plate, unfolding the plate and orienting the plate in a substantially linear configuration such that a bone contacting surface formed along a length of one surface of the plate is substantially in contact with the bone.

8. The method of claim 1, wherein the elongate plate is formed from at least one of a flexible mesh, a bioabsorbable material, and an osteoconductive material.

9. The method of claim 1, wherein affixing the elongate plate to bone in proximity to detached soft tissue using one or more bone fixation elements includes advancing each of the one or more bone fixation elements through a respective one of the plurality of openings.

10. The method of claim 1, wherein the one or more bone fixation elements are integrally formed with the plate, and affixing the elongate plate to bone in proximity to detached soft tissue using one or more bone fixation elements includes advancing the one or more fixation elements into the bone.

11. A surgical method, comprising:
delivering an elongate plate into a body of a patient to a tissue reattachment site in a delivery configuration in which the plate is folded;
affixing the elongate plate to bone in proximity to detached soft tissue using one or more bone fixation elements coupled to the plate and extending into the bone;
unfolding the elongate plate at one or more predetermined folding regions to bring a substantial portion of the surface area of the plate into contact with the bone; and
securing the detached soft tissue at a desired position relative to the bone using one or more suture strands extending from the elongate plate.

12. The method of claim 11, wherein the elongate plate is substantially rigid, and unfolding the elongate plate further comprises orienting the plate in a substantially linear configuration such that a bone contacting surface formed along a length of one surface of the plate is substantially in contact with the bone.

13. The method of claim 11, wherein the elongate plate is substantially flexible, and unfolding the elongate plate further comprises conforming a length of one surface of the plate to the bone such that the length is substantially in contact with the bone.

14. The method of claim 11, wherein a hinge is disposed at one or more predetermined folding regions, the method further comprising rotating a portion of the elongate plate about the hinge and towards the bone.

15. The method of claim 14, wherein the hinge is one of a living hinge and a barrel hinge.

16. The method of claim 11, wherein the elongate plate comprises at least two predetermined folding regions, the first predetermined folding region being disposed adjacent to an opening formed in a first end of the plate and the second predetermined folding region being disposed adjacent to an opening formed in a second, opposite end of the plate, and
wherein unfolding the elongate plate further comprises unfolding a first portion of the elongate plate by rotating the first portion at the first predetermined folding region and towards the bone, and unfolding a second portion of the elongate plate by rotating the second portion at the second predetermined folding region and towards the bone.

17. The method of claim 11, wherein the plate has one or more openings formed therein, each of the one or more openings having at least one suture strand extending therethrough.

18. The method of claim 11, further comprising drawing the detached soft tissue into contact with the elongate plate.

19. A surgical method, comprising:
delivering an elongate plate into a body of a patient to a tissue reattachment site in a delivery configuration in which the plate is folded;
affixing the elongate plate to bone in proximity to detached soft tissue using one or more bone fixation elements coupled to the plate and extending into the bone, the plate having a plurality of openings, and a plurality of suture strands extending from the plate along a length thereof, each of the plurality of openings having at least one of the plurality of suture strands extending therethrough;
prior to affixing the elongate plate, unfolding the plate and orienting the plate in a substantially linear configuration such that a bone contacting surface formed along a length of one surface of the plate is substantially in contact with the bone;
passing the suture strands through portions of the detached soft tissue and drawing the detached soft tissue into contact with the plate and the bone; and
securing the soft tissue with the suture strands at a desired position in contact with the plate and the bone.

* * * * *